(12) United States Patent
Abu-Akeel et al.

(10) Patent No.: US 11,154,375 B2
(45) Date of Patent: Oct. 26, 2021

(54) MEDICAL ROBOTIC WORK STATION

(71) Applicant: Brachium, Inc., San Ramon, CA (US)

(72) Inventors: Hadi Abu-Akeel, Fort Lauderdale, FL (US); George F. Wong, San Ramon, CA (US); Jonathan W. H. Wu, Pleasanton, CA (US)

(73) Assignee: BRACHIUM, INC., San Ramon, CA (US)

( * ) Notice: Subject to any disclaimer, the term of this patent is extended or adjusted under 35 U.S.C. 154(b) by 0 days.

(21) Appl. No.: 15/887,171

(22) Filed: Feb. 2, 2018

(65) Prior Publication Data

US 2019/0239969 A1    Aug. 8, 2019

(51) Int. Cl.
*A61C 5/77* (2017.01)
*A61B 34/37* (2016.01)
(Continued)

(52) U.S. Cl.
CPC ............ *A61B 34/37* (2016.02); *A61B 5/1172* (2013.01); *A61B 17/88* (2013.01); *A61B 46/13* (2016.02); *A61C 5/77* (2017.02); *A61C 7/002* (2013.01); *A61C 7/14* (2013.01); *A61C 7/146* (2013.01); *A61C 8/0089* (2013.01); *A61C 9/004* (2013.01);
(Continued)

(58) Field of Classification Search
CPC ......... A61C 5/77; A61C 8/0089; A61B 34/37; A61B 5/1172
See application file for complete search history.

(56) References Cited

U.S. PATENT DOCUMENTS 4,941,826 A * 7/1990 Loran .................... A61C 1/082
                                                      433/215
5,224,049 A * 6/1993 Mushabac .......... A61C 13/0004
                                                      264/222
(Continued)

FOREIGN PATENT DOCUMENTS

EP           1743594 A1     1/2007
WO      2016022347 A1     2/2016
WO    WO 2016/022347     *  2/2016

OTHER PUBLICATIONS

The Journal of the American Dental Association, "Robotics in Dentistry," Aug. 2001, vol. 132, No. 8, p. 1095.
(Continued)

*Primary Examiner* — Ralph A Lewis
(74) *Attorney, Agent, or Firm* — William J. Clemens; Shumaker, Loop & Kendrick, LLP (57) ABSTRACT

A medical robotic work station includes a frame and a robotic manipulator mounted on the frame for performing a treatment procedure on a patient seated in a chair adjacent the frame. The patient is in a seating posture and support locations are provided on the frame for resting bony members of the patient. Sensors track movement and position of the body members of the patient during performance of the treatment procedure by the robotic manipulator. The robotic manipulator is adapted to perform at least one of a medical, a dental, an ophthalmic and an orthopedic treatment procedure. A physician sits at a display monitor of a physician's work station for programming, monitoring and verifying a robot program for controlling the robotic manipulator to perform the treatment procedure.

22 Claims, 8 Drawing Sheets

(51) Int. Cl.
 *A61C 7/14* (2006.01)
 *A61C 9/00* (2006.01)
 *A61F 9/007* (2006.01)
 *A61G 15/12* (2006.01)
 *A61C 8/00* (2006.01)
 *A61B 5/1172* (2016.01)
 *A61B 46/13* (2016.01)
 *A61C 17/00* (2006.01)
 *A61B 17/88* (2006.01)
 *A61C 7/00* (2006.01)
 *A61B 34/30* (2016.01)
 *A61B 34/20* (2016.01)

(52) U.S. Cl.
 CPC ............ *A61C 17/005* (2013.01); *A61F 9/007* (2013.01); *A61G 15/125* (2013.01); *A61B 2034/2057* (2016.02); *A61B 2034/302* (2016.02); *A61B 2034/305* (2016.02); *A61C 2203/00* (2013.01)

(56) References Cited

U.S. PATENT DOCUMENTS

| | | | |
|---|---|---|---|
| 5,343,391 A | 8/1994 | Mushabac | |
| 5,347,454 A | 9/1994 | Mushabac | |
| 5,448,472 A | 9/1995 | Mushabac | |
| 5,545,039 A | 8/1996 | Mushabaac | |
| 5,562,448 A | 10/1996 | Mushabac | |
| 6,532,299 B1 | 3/2003 | Sachdeva et al. | |
| 6,640,128 B2* | 10/2003 | Vilsmeier | A61C 1/084 433/215 |
| 6,801,913 B2 | 10/2004 | Matsumura et al. | |
| 7,346,417 B2* | 3/2008 | Luth | A61B 34/20 700/117 |
| 7,455,520 B2 | 11/2008 | Sorensen et al. | |
| 7,625,208 B2 | 12/2009 | Warner | |
| 7,653,455 B2* | 1/2010 | Cinader, Jr. | A61C 1/084 700/119 |
| 7,742,635 B2 | 6/2010 | Rohaly et al. | |
| 7,907,166 B2 | 3/2011 | Lamprecht et al. | |
| 8,095,200 B2 | 1/2012 | Quaid, III | |
| 8,416,984 B2 | 4/2013 | Liang et al. | |
| 8,740,881 B2* | 6/2014 | Ortmaier | A61B 46/10 606/1 |
| 8,808,000 B2* | 8/2014 | Salcedo | A61B 1/24 433/75 |
| 9,259,291 B2* | 2/2016 | Gantes | A61C 1/084 |
| 9,390,063 B2* | 7/2016 | Hultgren | G06F 17/10 |
| 9,480,539 B2* | 11/2016 | Ortlieb | A61C 3/00 |
| 9,675,419 B2* | 6/2017 | Akeel | G16H 50/50 |
| 2001/0051881 A1 | 12/2001 | Filler | |
| 2002/0064759 A1 | 5/2002 | Durbin et al. | |
| 2002/0077542 A1 | 6/2002 | Vilsmeier et al. | |
| 2005/0186533 A1 | 8/2005 | Cohen | |
| 2007/0172803 A1 | 7/2007 | Hannaford et al. | |
| 2008/0081982 A1 | 4/2008 | Simon et al. | |
| 2010/0017032 A1 | 1/2010 | Dai et al. | |
| 2011/0039229 A1 | 2/2011 | Senia | |
| 2011/0256496 A1 | 10/2011 | Arzanpour | |
| 2012/0190981 A1 | 7/2012 | Harris et al. | |
| 2012/0231421 A1 | 9/2012 | Boerjes et al. | |
| 2012/0253360 A1 | 10/2012 | White et al. | |
| 2013/0039541 A1 | 2/2013 | Inazumi | |
| 2015/0057675 A1* | 2/2015 | Akeel | G16H 50/50 606/130 |

OTHER PUBLICATIONS

Xiaoyan Sun, et al., "Automated Dental Implantation Using Image-Guided Robotics: Registration Results," Int J CARS, 2001, vol. 6, pp. 627-634.

Allen Daniels, "The Future of Cosmetic Dentistry," Mar. 16, 2010, Retrieved from the Web: <guidetodentistry.com/the-future-of-cosmetic-dentistryi>.

The SensAble Dental Lab System Flyer, SensAble Techonologies, www.sensable.com, Copyright 2007.

* cited by examiner

MEDICAL ROBOTIC WORK STATION

FIELD OF THE INVENTION

This disclosure describes the configuration of a Medical Robotic Work Station (WS) for use in a medical facility equipped for robotic medical procedures. The following description uses, as an example, the application of the invention as a WS in a dentist's office wherein dental procedures are performed or assisted by an autonomous robot. However, the invention is not limited to the dental practice and can be applied readily as claimed in other medical fields.

BACKGROUND OF THE INVENTION

This section provides background information related to the present disclosure which is not necessarily prior art. This application particularly references an expired PCT application (PCT/US2015/042578) filed by one of the joint inventors and discloses an enhanced invention.

Medical robots may be categorized broadly as remote manipulators or autonomous robots. Remote manipulators have seen more common applications, but there are few examples of autonomous medical robots, some reduced to practice and others are still in the experimental phase. Examples of both categories are given below.

Remote manipulators, tele manipulators, or master-slave manipulators, are probably the common surgical robots in use today. One of the most successful commercial robots in this class is the da Vinci® robot (Intuitive Surgical, Sunnyvale, Calif., USA). In this master-slave system the surgeon sits at a master console next to the patient, who is operated on by the slave arms. The surgeon views the internal organs through an endoscope and, by moving the master manipulator, can adjust the position of the slave robot with higher accuracy and dexterity than humanly possible.

Autonomous and semi-autonomous systems are robots that can be preprogrammed to perform a procedure autonomously or share in a procedure with an operator by performing segments autonomously on command by the operator who may perform other segments. They have already been used in neurosurgery and orthopedics, mainly because the bony framework of these procedures offers a good material for registering the instruments. For example, the medical robot system from THINK Surgical, Inc., Fremont, Calif., is used for orthopedic surgeries, so far mostly for total knee arthroplasty and total hip arthroplasty, and performs some autonomous functions: the robot follows pre-planned cutting paths to perform planar cuts for a knee replacement and a cavity for a hip replacement without the surgeon's guidance. After the bone is milled, the surgeon continues the procedure manually. Another example, Cyberknife® from Accuray Inc. is used to deliver radiation doses to a brain tumor. It uses a robotic arm and a radiation source, which is mounted on the robot, to deliver radiation to the selected target following a programmed path. The position of the patient is located by image guidance cameras and the robotic arm is guided to precisely deliver small beams of radiation that converge at the tumor from multiple angles.

There's not much progress for the use of robots in dentistry although several approaches have been proposed without practical implementation. Of special interest is U.S. Pat. No. 6,640,128 describing a system wherein a dentist is assisted to perform dental procedure through visualization of the work space and its display on a monitor while his manual progress is compared with a planned path to allow the dentist to observe the deviation and make corrections to the path; the patent also suggests that a robot may substitute to do the dentist's manual work. U.S. Pat. No. 9,675,419, also naming the inventor, describes a System and Method for Automating Medical Procedures and outlines its application in dentistry.

Dentistry lends itself well to autonomous robotic procedures and promises appreciable benefits to patients and dentists alike. Dental procedures are performed mostly on teeth or gum sections that are externally visible or without deep intrusions into live tissues compared to other abdominal surgeries where manipulated robotic devices have been applied; thus posing much less risk and promises more accurate and cost effective treatment.

Figure 2A:
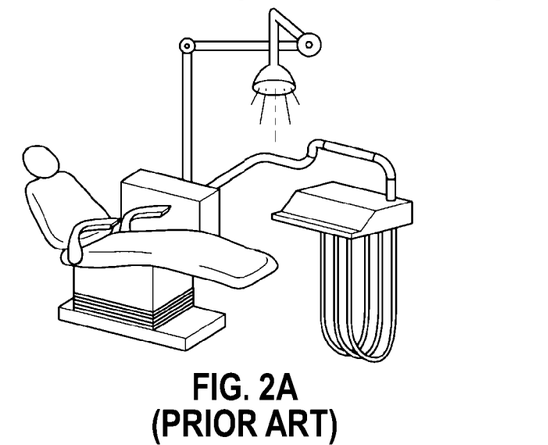
FIGS. 2A and 2B show conventional prior art dental chairs.
Figure 2B:
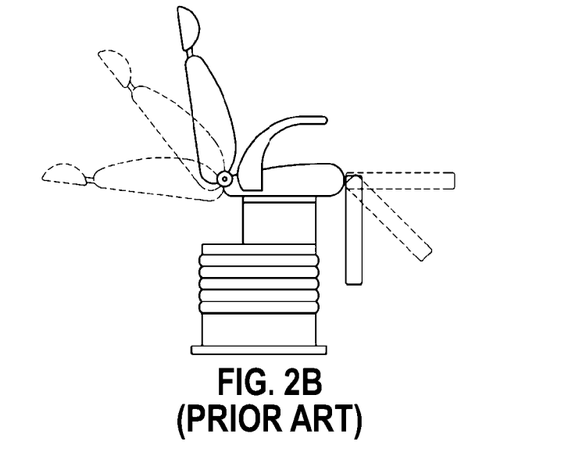

A WS used for robotic surgery need not replicate the environment used in medical practice for procedures performed by a physician. However, the '128 patent, suggesting one of the first autonomous robotic application in dentistry, still sits the patient in a supine posture on a conventional dentist's chair without consideration of the benefits of a change in the seating to suit robotic procedures; examples of conventional dental chairs are shown in FIGS. 2A and 2B of the drawings appended hereto.

Ergonomics of the layout of the medical work space are limited by human reach and their sensing, line of sight, dexterity, and the limitations of hand-eye coordination. The tools used for such procedures are also designed to be manipulated by a human hand; their size, form, weight and functionality are also tailored to the average person's capabilities. Accordingly such ergonomics, tools, and layouts cannot be optimal for any particular person and will generally impact negatively on the outcomes of many procedures. It would be, of course, ideal if all medical persons were of the same size, same dexterity, same acute sense of vision, hearing, touching, pressure, etc. It would also be ideal if all doctors had unlimited tolerance to tedious procedures that may take hours to complete under stress and not to have to take breaks or hand on the procedure to attending colleagues. On the other hand, robots offer those ideal advantages; their size can be tailored to the application with high dexterity, cameras can be located where needed for acute vision and views behind obstacles, sensors can be added with high sensitivity for pressure, sound etc. and they are oblivious to exertion or stress.

SUMMARY OF THE INVENTION

For all these advantages, this invention is targeted to enable the application of robotic medical procedures especially for autonomous robots that benefits from adding more structure to the robot's WS. Examples of such applications include dentistry, ophthalmology and orthopedics. Other medical applications may become obvious to those practicing in other field after recognizing the flexible features of this invention. For dentistry it includes tooling that facilitates the use of robots in dental application. Non-medical applications will benefit from some of the tooling included in this dental application but may require additional tools to support the particular application as needed.

The application of the invention to dentistry is described in detail in this patent application.

Typically, a WS in a dentist's office is designed to give the dentist access to the patient's jaws with convenience for the dentist, and less critically, for the comfort of the patient. The dentist performs dental procedures while the patient is reclined on a dental chair in a supine posture. This posture allows the dentist to look down into and access the patient's mouth. Lighting is provided by a device mounted above the patient's chair. This posture may be the most convenient choice for the dentist, if not the only one, but is less convenient to the patient who must cope with much discomfort. Dental processes require spraying water inside the mouth to clean debris and wash out any bleeding and excess saliva. Although the excess fluids are frequently sucked out with a vacuum tube inserted inside the mouth, they often choke the patient causing frequent interruptions to the dental procedure. The patient's reaction to pending choking often induces sudden movements that may expose the patient to the hazards of cuts and bleeding when the dentist does not react fast enough to withdraw the sharp dental tools. FIGS. 2A and 2B show examples of conventional dentist chairs with reclining and upright postures for some.

When dental procedures are performed robotically, as described in U.S. Pat. No. 9,675,419, the supine posture is not necessary for the robot to perform the procedures as it is for the dentist. Other postures are more convenient for robotic procedures as long as they allow access to the patient's mouth; a less hazardous and patient-friendly posture is desirable as described herein.

Figure 3:
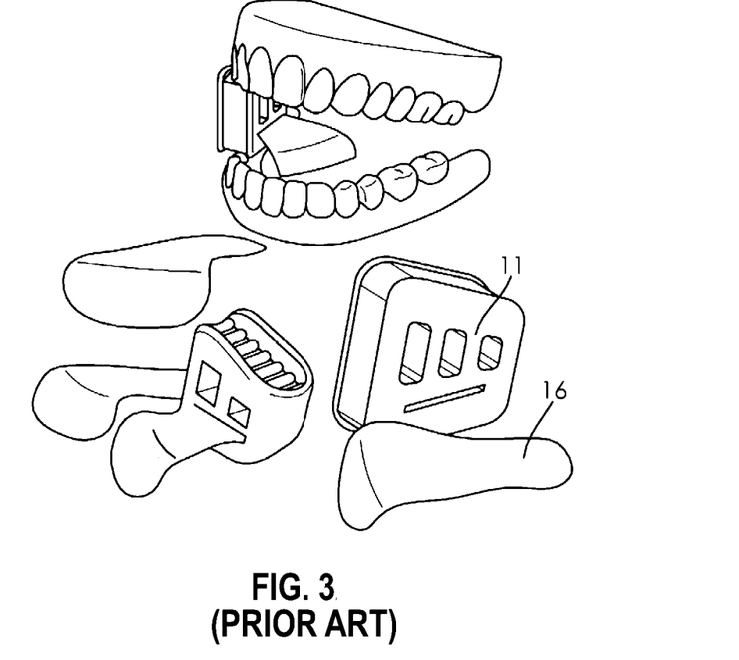
FIG. 3 shows conventional prior art wedge type mouth props and mouth guards.

Usually the dentist also fixes the opening of the patient's mouth with a mouth prop; in one form it's a wedge inserted on one side of the patient's mouth when procedures are performed on the opposite side. This prevents sagging jaws, closure of the mouth, and interruptions to the procedure. Conventionally, the mouth prop remains inside the mouth with only one function, propping the jaws open. Examples of wedge mouth props are shown in FIG. 3 which also shows the mouth prop fitted with flat plastic retainers that guard the patient's tongue from exposure to the sharp dental tools; other attachments may also be used to guard against fluid and debris scatter.

For some procedures the dentist may also insert a lip retractor, such the commercially available Optragate (registered trademark of Ivoclar Vivadent, Inc.), to keep the mouth open and provide good visual access to the teeth. Similarly the patient may be similarly fitted to help good visual access to the stations cameras to view and recognize the operating space of the robot.

This invention takes advantage of robotic capabilities to solve the problems associated with the manual aspects of the physician's practice, with focus here on dental practice. It seats the patient in a convenient upright position, which has no impact on the robot to work within the patient's mouth, and alleviates the problems of choking and injury. The invention also takes advantage of the ability to see inside the mouth with endoscopic or other miniature cameras with high resolution to enhance the accuracy of the procedure and improve patient safety. The optical system, made up of one or more sensors, can also collect various data before and after procedures are performed to allow repeatable quantifiable metric data points. These data points can be used at subsequent patient visits to modify and optimize patient treatment.

The invention also enables the use of robots in medical practice, and in particular dentistry, to allow the enhancement of dental tools to be made safer; with the consistency of the robots and the ability to reach locations inconvenient for the dentists, the tool can be optimized for the safety and performance rather than for the convenience of the dentist. By enabling robotic procedures the invention enhances the dental visit experience, long feared by many patients.

Robots can perform in more orientations and postures than humans. A dentist can only operate looking down into a patient's mouth because of his line of sight restriction and hand accessibility to the work space and tolerance to fatigue. A robot equipped with a computer vision system, is not limited to a particular line of sight into the patient's mouth since cameras can be located conveniently extraorally or intraorally as needed. The patient can be sitting comfortably upright in a chair and does not have to cope with choking on irrigation fluids and excess saliva. Any liquid will then self-discharge by gravity to the outside of the mouth and never reaches a choking level. Vacuum evacuation of liquids can then be done continuously and without interrupting the procedure or disturbing the patient as is conventionally practiced. The vacuum system can also be conveniently incorporated into the lip retractors.

Robots also perform best when their work space is constant and structured. If not, additional expense and complication is introduced to cope with a dynamic environment. Sensors are then required to sense patient movements and complicated software and controls provided for the robot to respond safely. If jaw and head constraints are applied to a patient in a supine posture they will add to existing discomfort and a feel of restraining confinement. With treatment with a current dentist, it is the dentist's ability to guess or estimate when the patient is uncomfortable and to stop treatment. In some cases the dentist may not stop treatment creating a very uncomfortable situation for the patient who is supine and not able to move away. This is most undesirable given the prevailing fear of visits to the dentist and is particularly impractical for children and restless patients.

However, with the person sitting upright, the person's forehead can be rested naturally and voluntarily against a comfortable support providing a good level of motion restraint without a feeling of confinement. With the head supported, patient's movement will be limited to much smaller disturbances and can be sensed by touch, vision or proximity sensors and reacted to by the robot safely and timely. With upright sitting and movements constrained to small amounts, the risk of cuts and bleeding is reduced appreciably and the choking is almost eliminated. This posture is commonly used for ophthalmology examinations without raising any patient concerns.

Alternatively, by fixing the mouth prop to a fixed frame and having the patient approach it voluntarily while sitting upright, it fixes the relative location of the lower jaw to the upper jaw within small tolerances, minimizes the movement of the target tooth, and structures the work space of the robot to a higher level. The robot can then have a common geometric reference with its target tooth to approach it accurately and perform a procedure such as for crowns, bracings, or implants. Robotic procedures can then performed more safely, more accurately and with much less technical complication of additional controls. With additional local sensing the robot accuracy and safety can be enhanced to unprecedented levels. For example, sensors can be added to sense movement of the teeth relative to the mouth prop and alert the robot to react by adjusting its path or stopping and withdrawing the tool. It may also be advantageous to use both approaches to head restraint, the mouth prop and the forehead, though the redundancy will have to be accommodated with adjustments. Without the use of a mouth prop an active vision system can also track patient movements within set parameters and beyond certain positional or motion limits the system can pause or stop. Software barriers programmed into the robot can provide further patient protection to never allow the treatment tool to enter into spaces of the patient that may cause pain or harm.

Dentists often interact with the patients to relieve their fears and alert them to pending sensations that may otherwise cause sudden reactions. Such reactions are often hazardous and may cause injuries from the sharp dental tools used or unintended disturbance to the tool to cause undue damage to patient's teeth, bone or gum. Robotic applications can be more successful by having an equivalent or better capability.

With a fixed head position, the dental work station can be equipped with audio and video screen monitor. The dentist's instructions and information can then be communicated to the patient and synchronized with the pending moves of the robot. These can be communicated with the dentist's voice and even as a video with his image and voice. This may include a patient heads up display. This heads up display may have the purpose of displaying images but may also serve as a protection barrier if the mouth is the intended work space. If other treatment spaces are worked on additional physical barriers may be utilized for patient safety.

Entertainment and soothing videos or other artistic displays may also be displayed thus calming the patient to make a dentist's office visit pleasant rather than arduous. Headphones, or speakers, providing soothing sound and music may also be attached to the head support structure. The headphones' strap may also wrap around the head to provide additional containment of the patient movements without undue discomfort. Noise cancelling technology can also be utilized to cancel machine noise such as a dental drill to create a calming and soothing environment for the patient.

With the mouth prop located on the opposite side of the tooth being operated on, it serves as an ideal location for lighting sources and miniature image sensors to provide close viewing of the work space opposite the mouth prop and inside the mouth. Other sensors, such as proximity sensors, may also be attached to the mouth prop inside the mouth or attached to the dental tools to sense exact tooth location and add accuracy to the robot's operations.

Figure 7:
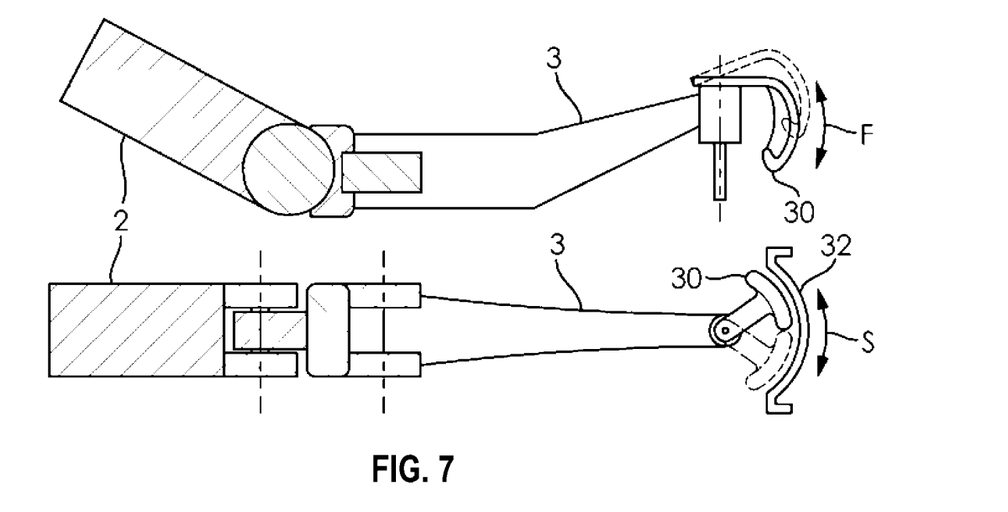
FIGS. 7 and 7A show a cheek guard for a robotic dental tool shown with limited swivel and elastic flex.

With robotic dental procedures and the ability to view in tight locations with miniature cameras and flexible lighting and imaging retrieval fiber optics, the patient cheeks need not be subjected to harsh stretching to expose the work space. Fiber optics in this application are not subject to the damaging effects of repetitive flexing, usually associated with their use and can provide access to unusually tight locations. The robot can be programmed using 3D imaging data of the jaws and its surroundings without such harsh stress. In performing the programmed procedure the robot can also access the work space at most teeth without stressing the cheeks. However, for safety and comfort of the patient the tool may also be fitted with soft, low friction guards that's either fixed to the tool or carried loosely to move with the tool as shown in FIG. 7. Those guards may also be fitted with lighting and image retrieval means to view the back side of the teeth for verifying the robot program or monitoring its operation. Conventionally the dentist uses mirrors and external lighting to view behind the teeth.

Obviously, there are many advantages to this invention and more will become apparent to the reader once the details of its construction are described and the complementary interactions among its elements are explained.

It should be noted that disposable barriers such as a plastic sleeve can be used for sanitation of the robot arm. An air curtain may be used to prevent aerosols generated from entering the housing of the robot. UV light disinfection may also be used as an option.

The work station may be supported with security data collection provisions to protect patient information and help with HIPPA compliance. This can include a biometric scan, UDB dongle and/or RFID so that without these things an unlicensed or untrained person cannot operate it. This also ensures that the correct patient is identified before treatment.

Additional biometrics data may be collected un-invasively such as fingerprint, heart rate, GSR (galvanic skin response), temperature, breathing rate, head acceleration (sudden jerks), etc. The fingerprint will be for patient identification and all the other sensor data will be for machine learning to improve the patient experience.

INVENTION OBJECTIVES

Therefore, it's among the objectives of the invention to provide a Medical Robotic Work Station that:
1. Is an enabler to autonomous medical robotic procedures;
2. Relieves the patient from the discomfort experienced during a conventional medical procedure;
3. Takes advantage of robotic capabilities to eliminate some of the difficulties associated with the use of robots in medical procedures;
4. Enhances the safety of the patient during a procedure;
5. Reduces the emotional strain on the patient;
6. Assures controlled location of the procedure target relative to the robot's operating space;
7. Provides a common geometric coordinate reference for the robot and the procedure target;
8. Minimizes the patient's tendency to move involuntarily with subsequent hazardous outcomes;
9. Allows convenient location of sensors close to the robot's work space;
10. Provides entertainment to help the patient endure or enjoy an otherwise arduous experience;
11. Includes tooling to support the needs of the application to benefit from the use of robots;
12. Provides means to guide the robot to recognize the patient and guides the robot to the target site of the medical procedure;
13. Provides safety means to mitigate autonomous robot operation hazards;
14. Provides patient-specific treatment;
15. Provides means to collect patient identification and biometric data to improve and personalize the treatment procedure;
16. Utilizes pre-treatment data to guide the treatment procedure; and
17. Utilizes the treatment data to augment pre-treatment data and to enhance future treatment procedures.

DESCRIPTION OF THE DRAWINGS

The above as well as other advantages of the present invention will become readily apparent to those skilled in the art from the following detailed description of a preferred embodiment when considered in the light of the accompanying drawings in which.

DESCRIPTION OF THE PREFERRED EMBODIMENT

The following detailed description and appended drawings describe and illustrate various exemplary embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical.

With dentistry as an example for applying the invention, this description will address its application to autonomous dental robotic procedures. Other medical procedures will have similar adaptations of what is described without deviation from the basic features or components described herein.

Figure 1A:
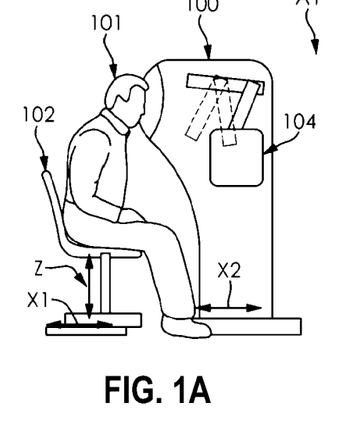
FIGS. 1A, 1B and 1C are views of a prior art Medical Robotics Work Station, including a robot work station A1 and a Physician's Work station A2 according to the invention.
Figures 1B, 1C:
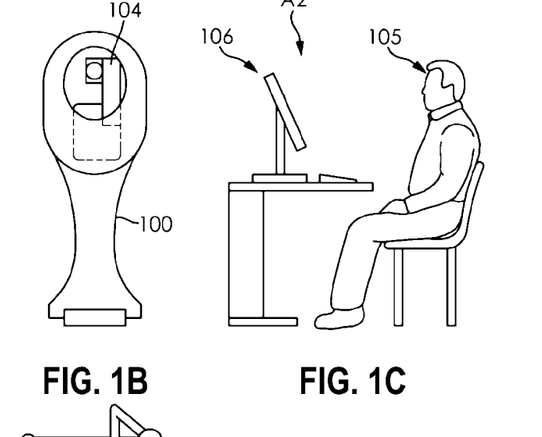

FIGS. 1A, 1B and 1C show a rendering of a general Layout of a medical robotic work station including a Physician's Work Station, PWS, A2 and a Robot Work Station, RWS, A1 within which a robot 104 is housed. A patient 101 is seated upright on a chair 102 that has means to rest his head on locations on a console 100. A physician 105 sits at a display monitor 106 for programming, monitoring and verifying robot programs as explained below. The patient's chair 102 is built such as it has vertical height adjustment Z and horizontal travel adjustment X1; X1 may be substituted by mounting the console 100 on a slide to provide an equivalent adjustment X2. The adjustments allow patients of different sizes to be seated with their head resting at head rests in the console 100. The Physician's WS A2 communicates with the Robot WS A1 over a cable data network or wirelessly. A physician may attend the PWS to monitor the autonomous robotic procedure, program the robot, or remotely guide the robot through a real-time procedure. It may be preferable for some procedures to be performed by the physician and assisted partially by the robot. The robot may perform its part autonomously or be remotely guided by the physician. The PWS will then include the master manipulator mechanism and the robot becomes the slave manipulator. The physician can observe the work space of the robot on the monitor 106 at the PWS and visually guide the robot 104 as appropriate.

Figure 4:
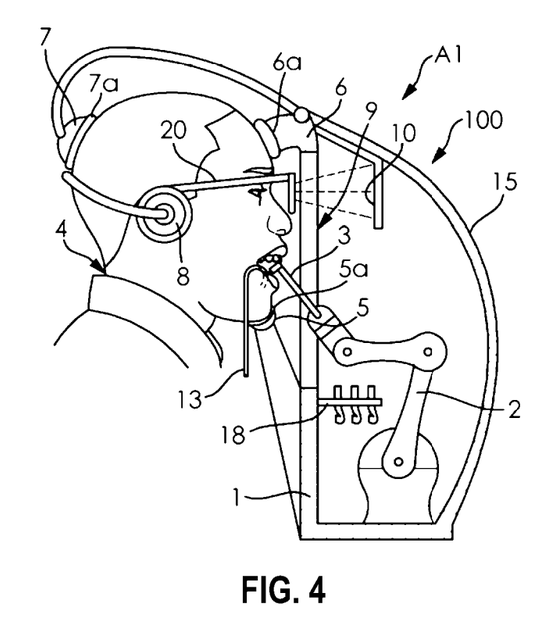
FIG. 4 shows the construction of the Dental Robotic Work Station according to the invention.
Figure 5:
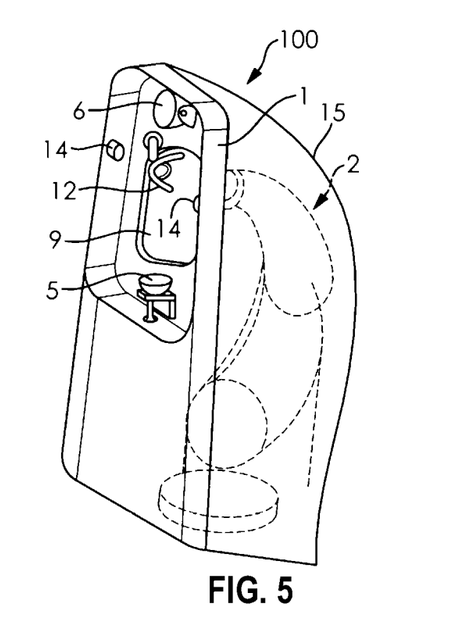
FIG. 5 shows a perspective view of the Dental Robotic Work Station.
Figure 8A:
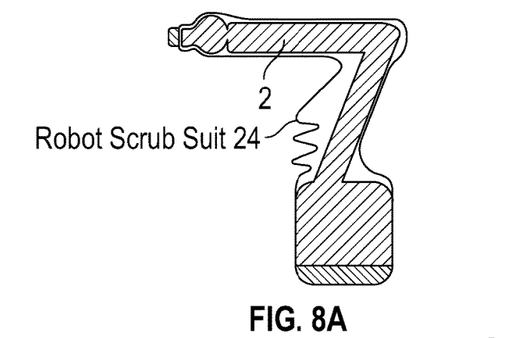
FIGS. 8A and 8B show sanitization approaches.
Figure 8B:
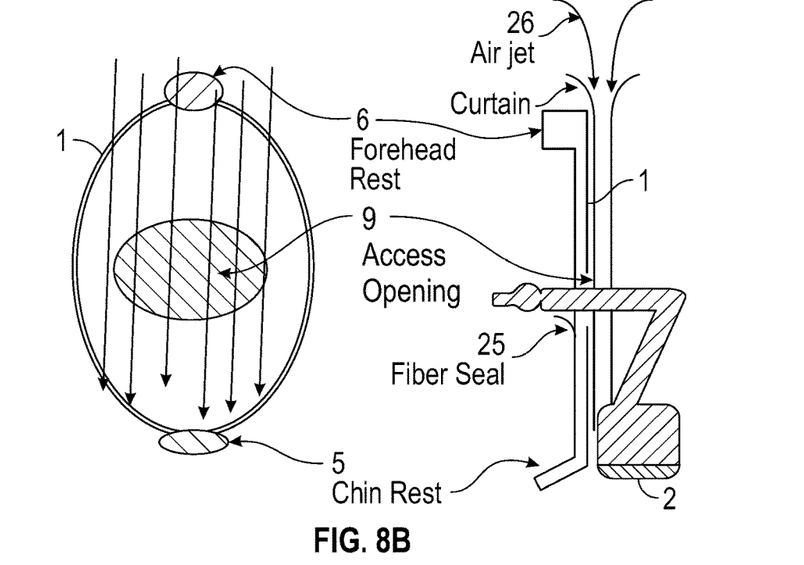

FIGS. 4 and 5 show the details of construction of the robot housing of the console 100 of the dental Robot Work Station A1. There is shown a frame 1, a robot 2 holding a dental tool 3 and operating inside the mouth of a patient 4. The patient is shown touching a chin rest or locator 5 and a forehead rest 6, having disposable liners 5a and 6a for patient sanitary protection and comfort. However, the chin rest 5 can be eliminated and the patient's chin located and tracked by sensors as shown in FIG. 8B. In the following description, the term "chin locator" is used to refer to the chin rest 5 and chin position sensors. There is also shown an optional head back support 7 with liner 7a to steady the location of the head in the back direction; a headphone 8 may also be attached to the back support 7 or to another location, or have wireless capability for audio information or entertainment. There's also an optional display system 10 attached to the forehead rest 6. Also the forehead rest can have biometrics sensors incorporated to measure things such as heart rate, galvanic skin response, temperature and etc. These sensors help the WS to monitor the patient and through machine learning build a patient-specific treatment plan. The head rest liners may be substituted by a head wrap, disposable or re-usable with sanitation that covers the head, forehead and chin.

The patient 4 is shown with his head upright rather than the conventional supine posture, thus allowing easy evacuation of annoying process fluids and debris. A vacuum evacuation tube 13 is shown with a terminal end placed at a level below the throat opening inside the mouth for suction of any saliva or irrigation fluids used for the process. A tool rack 18 is attached to the frame and carries a plurality of dental tools for use by the robot in different stages of a robotic procedure. An optional cover 15 may be removably attached to the frame 1 and encloses the robot. The cover 15 and the frame 1 can have a pleasantly styled exterior look to suit a usually clean and tidy medical environment. Alternately, for articulated robot manipulators, the outer shell 15 can be replaced with a stylish generally cylindrical cover that rotates with the first robot joint relative to the fixed robot base and having a narrow axial opening for the robot arms to path through. This embodiment has the advantage of reducing the size of the cover and the opening from which the robot arms access the treatment space. Also, a fingerprint sensor or other biometric sensors will be used to identify the patients.

The frame 1 encloses a multi-axes robot 2 mounted to the structure of the frame 1 at a location that allows the robot 2 to access a workspace inside the mouth that includes all locations for dental procedures. Frame 1 has an opening 9 between the chin locator and forehead rest, 4, 5, resp. through which the robot may access its workspace inside the patient's mouth. Although 6-axis robots are most common for doing a variety of manipulating tasks, it may be advantageous to use robots with five or less axes for some processes. Robots with articulated arms, as shown in FIG. 1, or others with Cartesian slides or with combination of mechanisms may be used and some may be preferred over others depending on the application and desired accuracy. The robot usually has a mechanism for moving the tool through the robot's workspace and another for its orientation. Articulated robot arms have one or two arms joined serially to a fixed base with rotary joints; the length of the arms and angles of motion determine the limits of the workspace where a tool can be delivered. The robot's wrist is its orientation mechanism and usually has one to three rotary joints, preferably with their axes of rotation orthogonal and intersecting, though not always. The wrist usually has attachment means, a gripper, to grasp or release a desired tool 3. The wrist of a dental robot is preferably small enough to introduce the tool inside the mouth and perform the dental process with adequate freedom to move and without interference with the jaw.

Tools for dental processes are relatively light, weighing few ounces, move only inside the mouth, and operate at relatively slow speeds compared to conventional industrial robot speeds. Hence, the robot can be small in size, low in power, and accordingly almost incapable of providing a threatening force to a human body. The sources of any hazard for a dental robot can be limited to the unavoidable presence of sharp and rotating tools. The hazard can be mitigated by assuring reliable robot performance, low speeds of operation, and reliable sensing of unexpected movements to deliver a timely mitigating response to the hazard. For better articulation and to avoid excess robot arm excursions, a 7-axis robot is advantageous. For example for teeth cleaning the 7-axis robot arm may make small movements in front of the patient while the wrist guides the tool around the teeth.

During a dental procedure, the robot may need different tools to operate with at different segments of the procedure; hence the WS includes a tool mounting rack 18, shown in FIG. 4, located for convenient access by the robot 2. The robot wrist may also be fitted, as often practiced, with tool-changing means—not shown—at the terminal end of the wrist. During operation the robot may reach to the Tool mounting rack 18, deposit a tool it may have and pick up another tool mounted on the rack; this procedure is known as a tool-change procedure.

The frame 1 also is shown with an optional display screen 10 in line with the patient's vision for viewing information on the progress of the procedure and display of entertaining or comforting videos that may help distract the patient's attention from the dental procedure and improve the patient's experience with dental visits. Together with the headphones the dentist may then communicate with the patient with assuring words and gestures as is practiced by experienced dentists. Alternately, the patient may wear a special type of glasses 20 (such as Google glasses) and have audio and videos streamed in for listening and viewing. Or the display 10 can be mounted on the forehead rest 6 with special lenses to project the image in a certain distance similar to VR/AR glasses.

Figure 6:
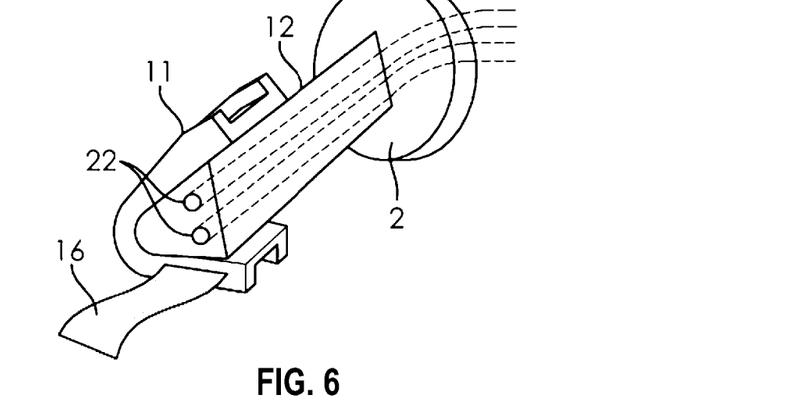
FIG. 6 shows a wedge type mouth prop applied to maintain jaw opening and location.

FIG. 6 shows a mouth prop 11 mounted on a holder 12 that extends from, and is attached, rigidly or flexibly, to the side of frame 1; mouth prop 11 allows the patient to tuck it firmly between the upper and lower jaws. It minimizes the movement of the teeth during the process. Mouth prop 11 is also fitted with a conventional tongue guard 16, shown in FIG. 3, to keep the tongue from intruding into the robot work space. Other attachments may be included for additional protection against fluids and debris that are used in conventional medical practice. Normally the robot can accommodate small movements through a well-known motion tracking software function and continue to operate with required accuracy, but may be commanded to stop automatically for gross movements. Since not all patients are of the same size, head restraints and jaw mouth prop locations 5, 6, 7 and 11 may be adjustable as well as the height of the patient's seat and its distance from the robot WS A1. Height and seat location adjustments are often available in conventional dental chairs. Only a chin adjustment may be necessary if the seat 102 has height adjustment; a chin rest may have a manual or automated adjustment controlled by a WS controller, not shown, or the robot controller. With the forehead and chin located by sensors, the mouth prop 11 may be left to float without the holder 12. No chin adjustment is necessary where the chin locator is embodied in position sensors. It should be noted that the chin locator can be a physical element moved to confine the chin sideways and sense its location by an embedded sensor or a remote sensor.

The mounting of the base of the robot 2, the mouth prop 11 and the holder 12 rigidly to the same frame 1 help to provide accurate registration between the robot and the patient's jaws and minimizes the need for frequent calibration of the robot relative to its work space. However, it may be necessary to float the mouth prop and track its location. The robot is still fitted with (vision and mechanical) tracking capability that allows it to sense and track any movement in its work space and adjust its path accordingly, hence maintaining the desired accuracy. The tracking function is a common robotic practice utilizing sensors to measure the movement of the tracked object and signal the robot controller with magnitude and coordinates of the movement to add or subtract from the programmed path of the robot. It is employed in many Industrial robot applications and is usually available within the robot controller's software. If the holder 12 is floating or flexibly attached to the frame 1, their relative location and orientation can be monitored my sensors to help with the tracking function. A 3D camera system may be inserted inside the mouth that allows the robotic arm to calibrate against a known past scanned surface and take an identical picture for accurate and repeatable data capture and historic dental health comparison.

FIG. 5 shows an isometric view of the jaw location environment including the forehead, chin and jaw locators 6, 5 and 12 respectively. The chin rest 5 may be made adjustable to accommodate different head sizes. The jaw holder 12 may be placed on either side of the opening 9 opposite to the side of the jaw where the robot operates. The chin rest includes a chin location sensor that tracks the chin and the location of the lower jaw relative to the upper jaw. The chin location sensor also monitors the presence of the patient's chin such as if the patient moves away from the sensor a signal is generated and used to prevent robot operation or stop an active procedure from continuing.

There also is shown two cameras 14 placed at the sides of the opening 9 in frame 1; the cameras help provide images of the processing area of the robot as it enters through the space 9 and approaches the target tooth of the procedure. The cameras may be fitted with lighting Illuminators to project a light with a wavelength spectrum suitable to reflect from the work space and to assure good image quality. Other sensors may be mounted to the frame 1 in proximity to the work space of the robot to measure relative location of the robot to elements in the workspace, help the robot track different element locations, and improve accuracy and safety. In another arrangement shown in FIG. 6, fiber optic cables 22 may be used to transmit light to the work space and images back through the holder 12 or along its sides, to camera electronics located remotely, such as with commercial endoscopes. One cable 22 usually transmits light from an LED source to the workspace and the other is fitted with an objective lens or a lens stack to receive the image in its field of view that's transmitted back along the fiber to a CMOS video chip located remotely. Endoscopes are commonly used in medical and industrial practice to snake a fiber optic cable through tight spaces and observe the interiors of cavities on a monitor. Industrial endoscopes have cables of about 5 mm diameter or larger and medical ones can be smaller than 2 mm in diameter. Alternatively, the miniature camera may be located on the mouth prop and its data communicated externally to the robot controller. The work station is provided with cameras and mounted either stationary or on the robot arm 2, see camera 27 in FIG. 9, such that the cameras can be manipulated to have visual access to the front of the head of the patient 4. The camera 27 is located such that both the lower and upper jaws can be in view for identification of their features and help guide the robot to the mouth opening and along the contours of the jaws to perform a continuous a path process such as cleaning the teeth or 3D scanning of the dental arch.

FIGS. 4 and 5 show an arrangement with an upright head orientation, however, the WS may have different forward head-tilt angles for the comfort of the patient. The work station A1 also includes a chair for seating the patient. It may also be provided with a slide track to move the chair or the frame 1 along a track for ingress and egress and to accommodate patients having long or short legs. The work station can also be provided with chair height adjustment as often found in conventional office and medical chairs. The chair may be a conventional dentist's chair if it provides an upright posture and vertical height adjustment.

Figures 12A, 12B:
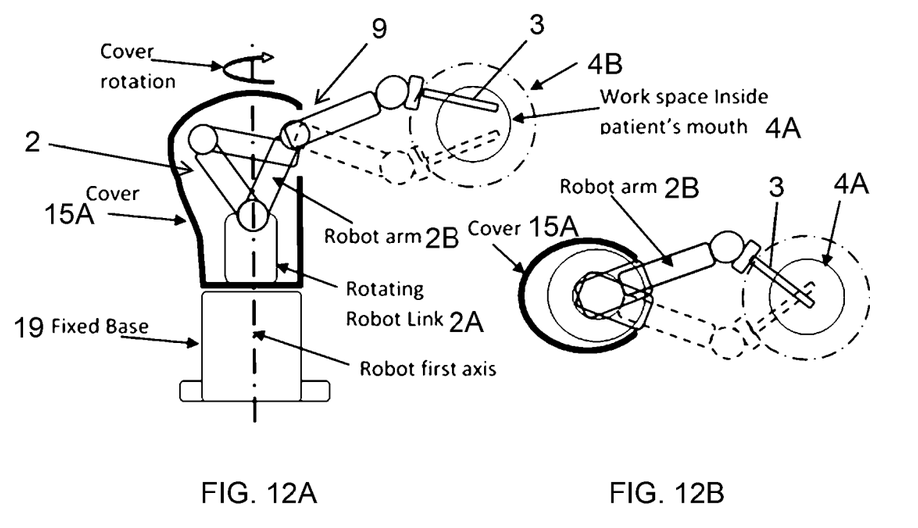
FIG. 12A is a side elevation view in partial cross-section and FIG. 12B is a top plan view in cross-section of an alternate embodiment Dental Robotic Work Station according to the invention.

The optional outer shell 15 encloses the robot 2 and latches to the frame 1 at several locations to provide esthetic and pleasing appearance suitable for a medical environment. The latches are releasable for access to the robot 2 and the dental tool change bracket 18 for maintenance and adjustments. Alternately, as shown in FIG. 12A and FIG. 12B, for articulated robot manipulators 2, the outer shell 15 can be replaced with a stylish generally cylindrical cover 15A that rotates with the first robot joint (rotating robot link 2A) relative to the fixed robot base 19 and having a narrow axial opening 9 for the robot arm 2B to pass through. This embodiment has the advantage of reducing the size of the cover and the opening from which the robot arms access the treatment space. The robot arm 2B moves the dental tool 3 within a work space 4A inside the patient's mouth 4B.

For sanitary protection the robot 2 may be covered, from the tool gripper all the way to its base with a protective "gown" 24, like a scrub suit (see FIG. 8A), to keep the robot from carrying contaminations from one procedure to another and the gown changed for each procedure. The gown 24 may be disposed of or sanitized. Of course all the elements of the work station should be designed such as to be easy to clean and sanitize as practiced with other medical equipment. Contamination may also be avoided by minimizing the size of the opening 9. Alternately, only extremities of the robot arm and the tool may be covered with disposable or sanitized covers.

The interior of the shell 15, including the robot 2, may also be isolated from the outside environment by closing the opening 9 by other means. For example a re-sealable or stretchable membrane or expanding sleeve that the robot penetrates and is sealed by a tool flange as the robot introduces the tool into its work space. This configuration encapsulates the entire rest of the robot for infection and bacterial control.

Another means of isolation is to cover the opening 9 with an air jet or curtain 26 (see FIG. 8B) that allows the robot 2 to penetrate through while keeping surrounding air out with any carried contaminants. Another means is a curtain or seal 25 of radial fibers (see FIG. 8B) that closes the opening 9 and still allows the robot 2 to penetrate through while the fibers seal around the robot arm.

Adjustments to the headrests, the chair location and height may be manual or motorized and possibly controlled by a digital controller such as the robot controller.

Usually a dentist may use stretchers and clamps, hooks, or his fingers, to stretch the patient's cheek away from the teeth and out of his line of sight. This of course is not advised with robot operations and an appropriate alternate is provided by the invention.

Figure 7A:
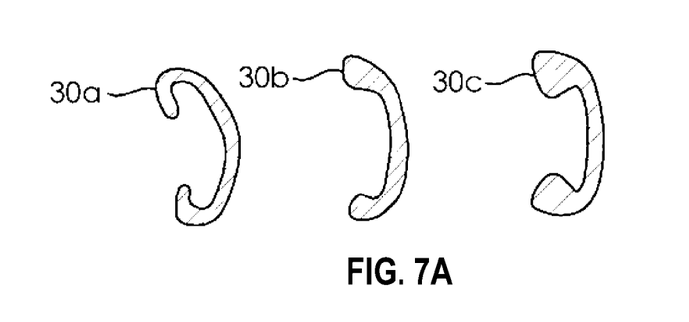

FIGS. 7 and 7A show a cheek guard as a substitute in the invention for this function by attaching a shroud 30 to the tool 3. In one form, the shroud 30 is hinged to the top of the tool 3 to swing freely within a limited range S indicated by its solid and dotted outlines, and it may have a spring return. The center of the swing may be fixed at any angle depending on the direction of introducing the tool into the mouth and its range of angular movement. As the tool is introduced sideways, the guard 30 protects the cheek skin 32 from tool intrusions and may push the cheek gently outwards if more space is needed. This is much gentler than current stretching practice and is possible because the robot vision is enabled from the other side of the mouth by means of the cameras 14. As the tool is moved along the robot path it may tilt or displace in all directions, hence the shroud surface has easy spherical surface and made of low friction material adept to sanitization chemically or by autoclave as may be medically acceptable. The shroud 30 is also shown to have flexing capability indicated by the arrow F to reduce the pressure on the gum if the tool pushed the shroud against it. The stiffness of the shroud in flexing can be designed to keep the pressure on the gum within comfortable limits. The form of the shroud may be chosen to also allow low-force deformability if squeezed sideways as proposed with three cross-section options in FIG. 7A. The guard 30 may also be fitted with fiber optics that illuminate and retrieve images of the outer tooth side adjacent to the cheek if needed. Tool guards may not be necessary for continuous path procedure such as cleaning, oral imaging and scanning; the tool is usually of smooth non-obtrusive geometry and is separated from the teeth and gums by adequate space similar to a tooth brush. The process is non obtrusive and reversible since no tissue or bones are modified in such procedures. The tool may also be covered with a softer material such as a rubber or plastic to enhance safety.

Figure 10:
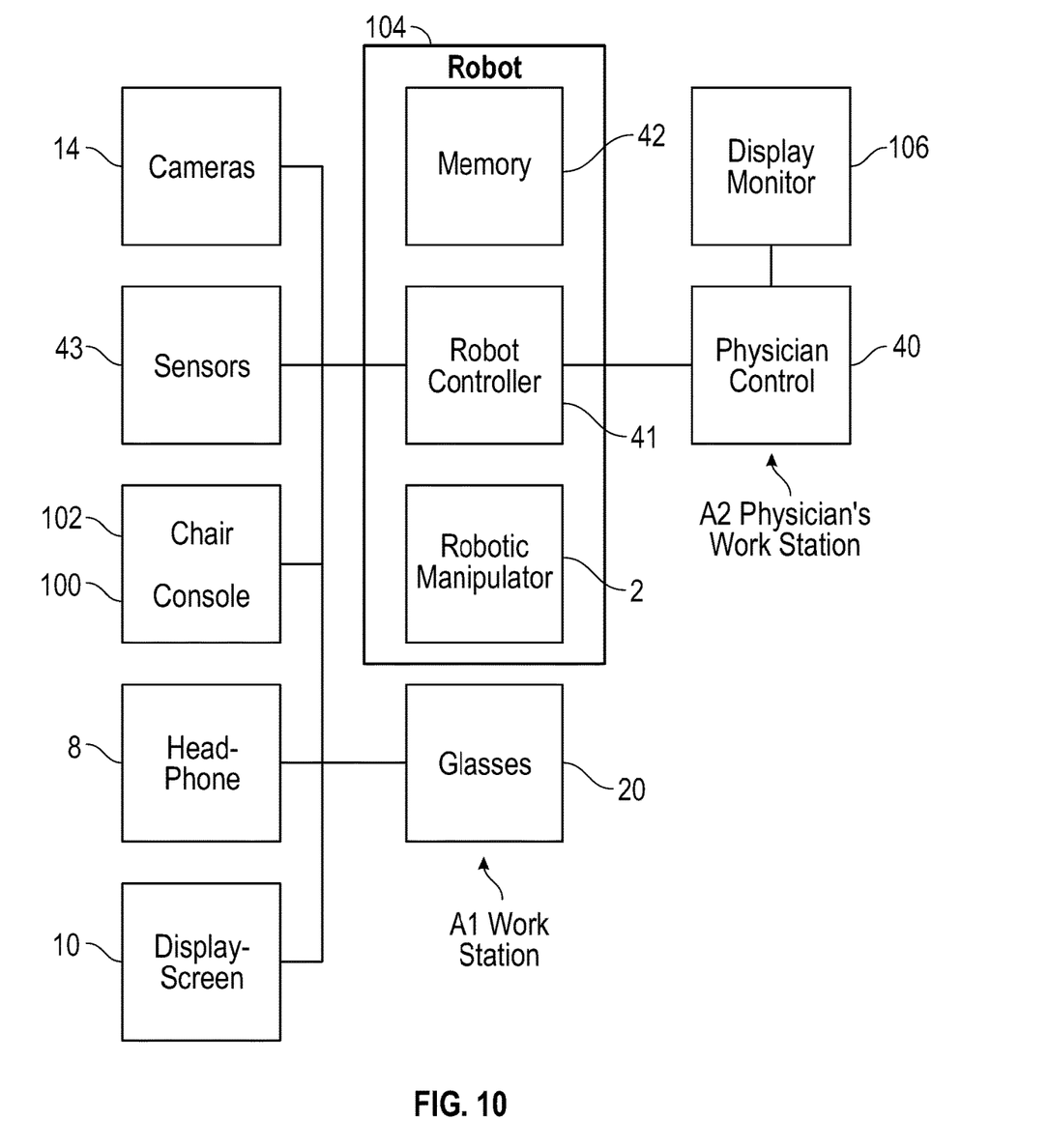
FIG. 10 shows a schematic block diagram of the control system for the medical robotics work station according to the invention.

FIG. 10 shows a schematic block diagram of the control system for the medical robotics work station including the robot work station (RWS) A1 and the physician's work station (PWS) A2. The PWS A2 includes the display monitor 106 connected to a physician control 40. The control 40 can be a computer adapted to exchange information with the RWS A1. The robot 104 includes the robotic manipulator 2 and a memory 42 connected to a robot controller 41. The memory 42 stores data and a software program for controlling the robotic manipulator 2 during the treatment procedure. The controller 41 is connected to various devices in the RWS A1 for data exchange by any suitable means such as a bus, a wired network or a wireless network. The devices include the cameras 14, sensors 43, the console 100, the chair 102, the headphone 8, the display screen 10 and the glasses 20.

It should be noted that the workability of some of the novel aspects of the invention will be enabled by several other practices employed conventionally to enhance its practicality; for example, air jets may be used to clear the view for the cameras or fiber optic ends, normally practiced sanitization techniques such as autoclaves and antibiotics will be used for the environment and associated tools and structures, etc.

Figure 9:
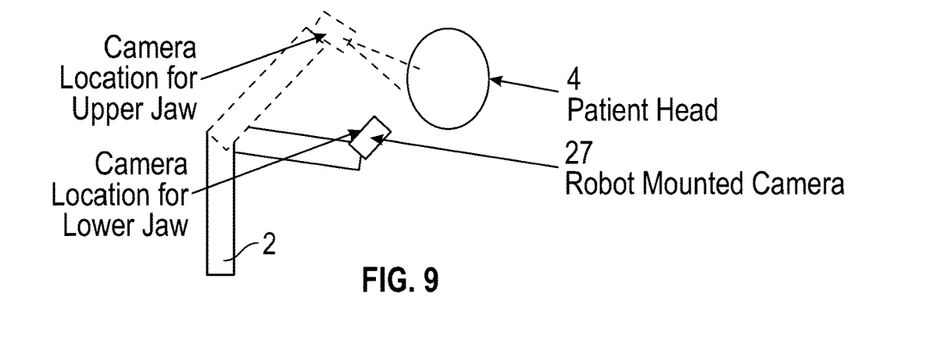
FIG. 9 shows a camera mounted on the robot and manipulated to recognize the upper and lower jaws of the patient.

The utility of the invention is best illustrated by an example of a dental process utilizing the invention; and is hereby explained. The robot can be fitted with a dental hygiene spray cleaning tool, a 3-D scanner, a drill, etc. to perform a dental procedure. The patient sits on the seat of the work station with the forehead resting on the headrest, an operator adjusts the chin locator to the bottom surface of the patient's chin and initializes the system to operate. Alternately, the chin locator can be powered to move to the chin location as guided by a digital controller. Once seated, signals must be detected by the controller 41 of the presence and appropriate seating of the patient, the jaw recognition camera(s) 27 then take 3D images of the two jaws to locate them relative to the robot and identify their geometry to enable the robot to be programmed. It is preferable that one 3D vision camera 27 mounted on the robot 2 be manipulated to two different locations for best visualization of each jaw.

Figure 11A:
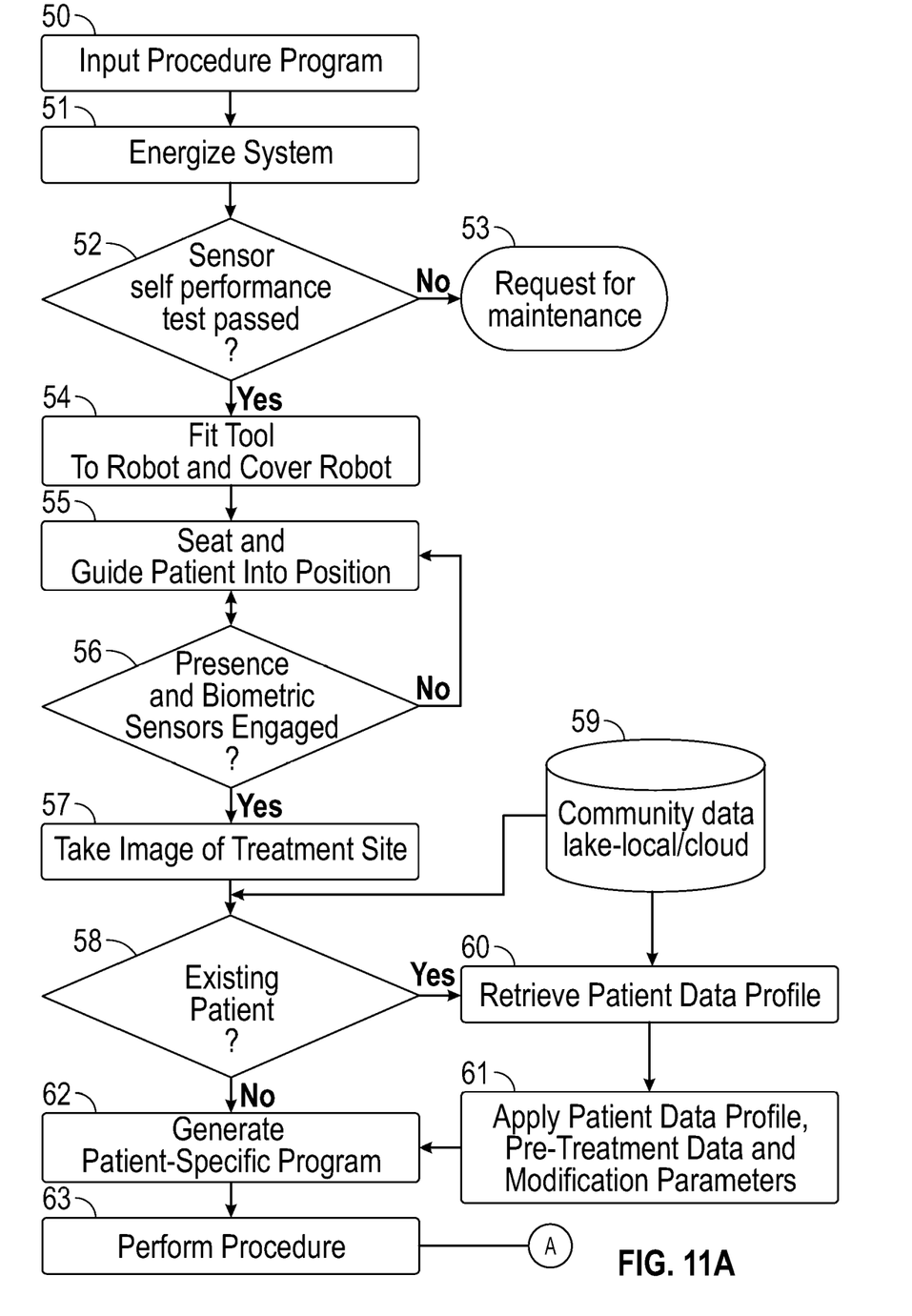
FIG. 11A and FIG. 11B are a flow chart illustration of the method according to the invention.
Figure 11B:
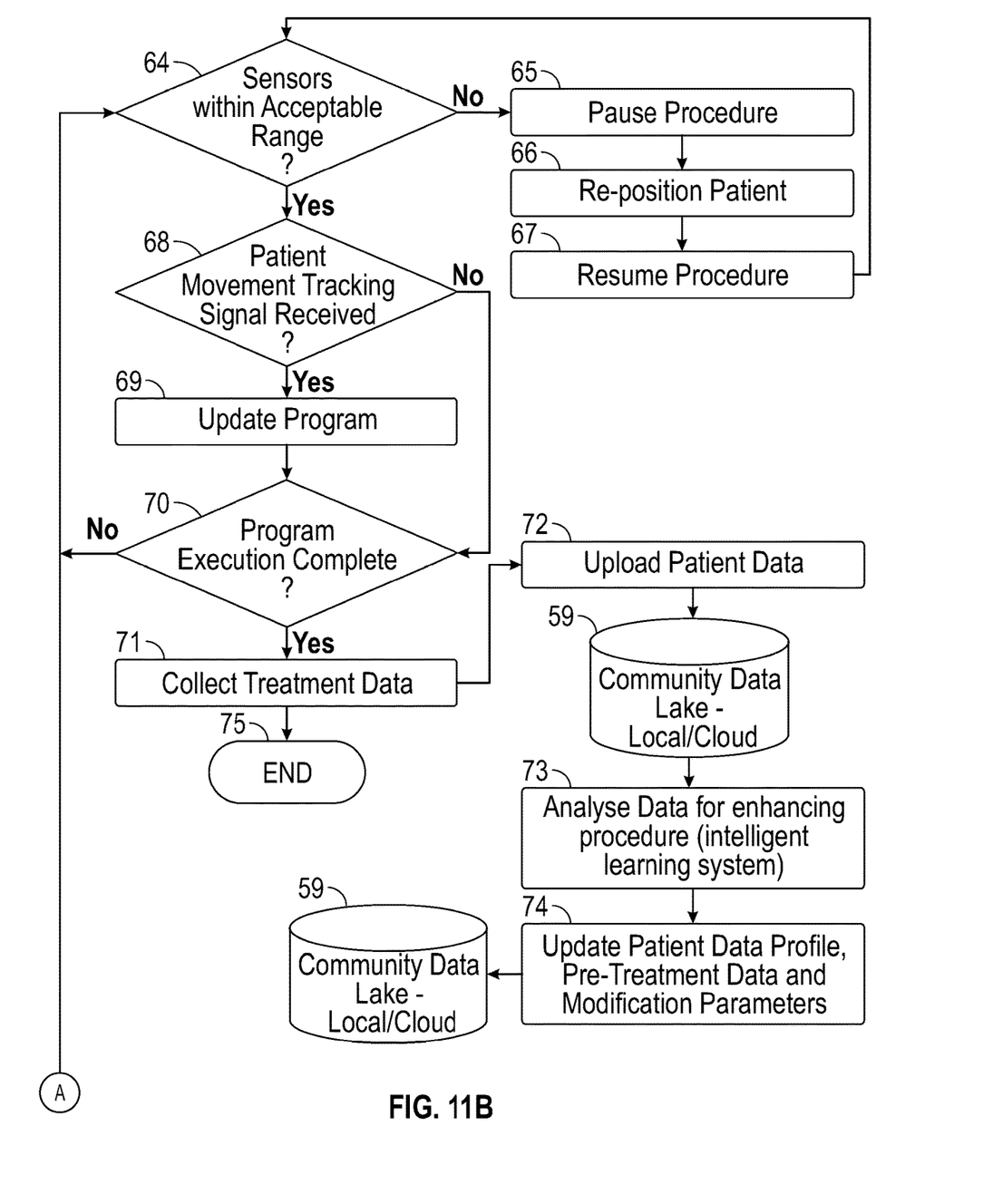

An applicable method for performing a treatment procedure autonomously according to the invention is depicted in the flow chart illustrated in FIG. 11A and FIG. 11B. The method starts at a step 50 "Input Procedure Program" wherein the software program for a selected medical procedure is either loaded into the memory 42 (FIG. 10) or selected from several different procedure programs stored in the memory. Next the robotic system is energized in a step 51. All of the sensors 43 are checked in a step 52. A system wide check of all sensors, not exclusive to 43, perform a self-performance test to ensure all sensors are working. If any of the sensors indicate a problem, the method exits the step 52 at "NO" and the system would send out a request for service in step 53. If all the sensors pass the self-performance test, the method exits the step 52 at "YES" and proceeds to step 54 where a selected tool is fit to the robot and the robot is covered.

In a step 55, the patient is seated in the chair 102 (FIG. 1A). Next, in step 56, biometric and presence sensors, such as a forehead sensor 43 (FIG. 10) detects whether the forehead of the patient is correctly positioned in the forehead rest 6 (FIG. 4) or a chin sensor 43 (FIG. 10) detects whether the chin of the patient is correctly positioned in the chin rest 5 (FIG. 4) or at the chin locator. If either condition is "NO", the method loops back to the step 55 to adjust the patient's position. When the patient is correctly positioned, the method exits the step 56 at "YES".

At step 57, the robot system takes an image of the site where the medical procedure is to be performed. At step 58, the system searches the Community Data Lake in step 59 to check if the patient exists in the Community Data Lake. If the patient exists in the Community Data Lake, the method exits step 58 at "YES" to step 60 where the patient data profile is retrieved. The method then takes the patient data profile, pre-treatment data and modification parameters and applies them to the system in step 61. The method then proceeds to generate a patient-specific program in step 62 which can also be reached if the patient is not found in the Community Data Lake at step 58 and exits step 58 at "NO". Now the robot system begins the medical procedure in a step 63 according to the patient-specific program generated in the step 62. In a step 64, a check is made to confirm that the sensors data are within acceptable range. If at least one sensor is not in an acceptable range, the method exits the step 64 at "NO" and pauses the procedure at step 65. The patient is allowed or helped by repositioning at step 66 to operating limits. The method then proceeds to step 67 which resumes the procedure and returns to step 64.

When all of the sensors are within acceptable range, the method exits the step 64 at "YES" and checks for a tracking signal being received in a step 68. If the tracking signal is not received, the method exits the step 68 at "NO" and continues at a step 70. If the tracking signal is received, the method exits at "YES" to update the patient-specific program at a step 69 and then enter the step 70. The method then checks if the patient-specific program execution is complete. If it is not complete, the method exits step 70 at "NO" and loops back to step 64. If it is completed, the method exits step 70 at "YES" and proceeds to collect treatment data at step 71. The method then uploads the patient data at step 72 to the Community Data Lake at step 59. The method also exits step 71 to step 75 where the medical procedure is finished. The Community Data Lake at step 59 will continuously analyze data for enhancing procedure using its intelligent learning system at step 73 and update the patient data profile, pre-treatment data and modification parameters at step 74 in the Community Data Lake at step 59.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A robotic work station having a frame supporting an autonomous or remotely guided robotic manipulator and a chair for seating a patient during a treatment procedure performed by the robotic manipulator comprising:

the chair being configured to seat the patient in an upright posture in proximity to the frame;

means for supporting bony members of the patient, which bony members locate a work space;

a plurality of sensing means for monitoring a location of the work space relative to the robotic manipulator;

a sensing means for identifying features of the work space;

a means for sensing a location of the work space relative to the robotic manipulator;

a means for generating a patient specific software program autonomously based on a selected treatment procedure program, the location of the work space and the features of the work space;

a cover for sanitary isolation of the robotic manipulator from the patient;

an opening formed in the cover for the robotic manipulator to access the work space and perform the treatment procedure; and wherein the robotic manipulator is guided into the work space in response to signals generated by the means for sensing a location and is guided to perform the treatment procedure autonomously according to the patient specific software program.

2. The robotic work station according to claim 1 including at least one of a means for imaging a treatment site of the patient, a means for sensing a presence or an absence of the patient at the chair, a means for pausing or stopping the performance of the treatment procedure by the robotic manipulator in response to a command or a signal from a sensor, and a means for tracking and responding to movement of body members of the patient during the performance of the treatment procedure.

3. The robotic work station according to claim 1 wherein the treatment procedure is one of a medical, a dental, an ophthalmic and an orthopedic treatment procedure, and wherein the dental procedure is one of cleaning, scanning, bracket placement, crown milling and tooth implant.

4. The robotic work station according to claim 1 including a means for collecting biometrics data from the patient using sensors when the patient is seated in the chair.

5. The robotic workstation according to claim 1 including a means for identifying the patient using a biometric sensor to collect a fingerprint of the patient.

6. A robotic work station for seating a patient during a treatment procedure comprising:

a robotic manipulator mounted on a frame for autonomously performing the treatment procedure;

a chair for seating the patient in a seating posture in proximity to the frame;

a means for supporting bony members of the patient, which bony members locate a work space;
a means for sensing autonomously a location of the work space relative to the robotic manipulator;
a camera mounted on and manipulated by the robotic manipulator for imaging selected features of the work space when the patient is seated on the chair;
a gown covering the robotic manipulator for sanitary isolation of the robotic manipulator from the patient; and
wherein the robotic manipulator is guided to autonomously perform the treatment procedure on the patient, according to a patient specific software program generated autonomously based upon a selected treatment procedure program and the selected features of the work space, with surgical tools in response to signals generated by the means for sensing and the camera and is guided into the work space in response to the signals generated by the means for sensing.

7. The robotic work station according to claim 6 wherein the treatment procedure is one of a medical, a dental, an ophthalmic and an orthopedic treatment procedure, and wherein the dental procedure is one of cleaning, scanning, bracket placement, crown milling and tooth implant.

8. The robotic work station according to claim 6 including a tool rack mounted on the frame for exchanging tools during the performance of the treatment procedure.

9. The robotic work station according to claim 6 including audio-visual means for instructing, informing or entertaining the patient during the performance of the treatment procedure.

10. The robotic work station according to claim 6 wherein the cover is supported by the frame, the robotic manipulator being positioned inside the cover and the cover being styled esthetically for appeal in a medical environment.

11. The robotic work station according to claim 6 wherein the robotic manipulator has an arm with articulated joints or sliding members for positioning a wrist mechanism of the robotic manipulator.

12. The robotic work station according to claim 6 wherein at least one of the chair and the means for supporting is adjustable relative to the frame.

13. The robotic work station according to claim 6 including a physician's work station connected to a controller of the robotic manipulator for at least one of monitoring, guiding and programing movement of the robotic manipulator.

14. A method for performing a treatment procedure autonomously at a work site of a patient seated in an upright posture using a medical robotic work station, the work station including a robotic manipulator connected to a robot controller and a plurality of sensors comprising the following steps:
  a. inputting a procedure program corresponding to the treatment procedure into the robot controller;
  b. fitting the robotic manipulator with a tool appropriate for performing the treatment procedure;
  c. seating the patient at the work station facing the robotic manipulator with a bony member of the head of the patient resting on a support of the work station;
  d. adjusting a chin locator to touch a bottom of a patient chin with a mouth of the patient being open;
  e. energizing the robot controller and the robotic manipulator to perform the treatment procedure autonomously;
  f. detecting signals from the sensors indicating a presence of the patient seated in the upright posture and with the mouth open;
  g. taking an image of the work site with a camera to identify a geometry and location of the work site relative to a location of the robotic manipulator;
  h. using the image to autonomously generate a patient-specific program from the procedure program to suit the geometry and features of the work site; and
  i. performing the treatment procedure autonomously wherein the robotic manipulator manipulates the tool according to the patient-specific program.

15. The method according to claim 14 including a step of identifying the patient through biometric sensing prior to performing the treatment procedure.

16. The method according to claim 14 including populating and using a data base of treatment procedures to enhance the procedure program.

17. The method according to claim 14 including using sensors to track patient movements and manipulating the tool to maintain desired relative tool-patient positions according to the patient-specific program.

18. The method according to claim 14 including using sensors to signal the robotic manipulator to track, pause or stop performing the treatment procedure for safety of the patient.

19. The method according to claim 14 including applying a patient data profile, pre-treatment data and modification parameters associated with the patient to generate the patient-specific program.

20. The method according to claim 19 including collecting treatment data generated by the performing of the treatment procedure and using the treatment data to update at least one of the patient data profile, the pre-treatment data and the modification parameters.

21. The robotic work station according to claim 1 wherein the robotic manipulator is mounted on a fixed base to rotate about a first axis, the cover is mounted to rotate with the robotic manipulator about the first axis and a robot arm of the robotic manipulator extends through the opening in the cover.

22. A method for performing a robotic procedure autonomously at a work site of an object including a robotic manipulator connected to a robot controller and a plurality of sensors comprising the following steps:
  a. inputting a procedure program corresponding to the robotic procedure into the robot controller;
  b. fitting the robotic manipulator with a tool appropriate for performing the robotic procedure;
  c. locating the object at the work site within reach of the robotic manipulator;
  d. energizing the robot controller and the robotic manipulator to autonomously perform the robotic procedure;
  e. detecting signals from the sensors indicating a presence of the object;
  f. taking an image of the work site with a camera to identify a geometry and location of the object within the work site relative to a location of the robotic manipulator;
  g. using the image to autonomously generate an object-specific program with the robot controller from the procedure program to suit the geometry and features of the object and the work site; and
  h. performing the robotic procedure autonomously wherein the robotic manipulator manipulates the tool according to the object-specific program.

* * * * *